(12) United States Patent
Mandic et al.

(10) Patent No.: US 8,247,567 B2
(45) Date of Patent: Aug. 21, 2012

(54) PROCESS FOR SOLVENT REMOVAL FROM OMEPRAZOLE SALTS

(75) Inventors: Dejan Mandic, Ljubljana (SI); Renata Toplak Casar, Logatee (SI)

(73) Assignee: Lek Pharmaceuticals, D.D., Ljubljana (SI)

( * ) Notice: Subject to any disclaimer, the term of this patent is extended or adjusted under 35 U.S.C. 154(b) by 410 days.

(21) Appl. No.: 12/523,025

(22) PCT Filed: Jan. 9, 2008

(86) PCT No.: PCT/EP2008/050198
§ 371 (c)(1),
(2), (4) Date: Aug. 26, 2009

(87) PCT Pub. No.: WO2008/087081
PCT Pub. Date: Jul. 24, 2008

(65) Prior Publication Data
US 2010/0076025 A1  Mar. 25, 2010

(30) Foreign Application Priority Data
Jan. 18, 2007  (EP) .................................... 07100738

(51) Int. Cl.
*C07D 401/12*  (2006.01)
(52) U.S. Cl. .................................................. 546/273.7
(58) Field of Classification Search ................ 546/273.7
See application file for complete search history.

(56) References Cited

FOREIGN PATENT DOCUMENTS

| | | |
|---|---|---|
| CA | 2166794 A1 | 1/1995 |
| CA | 2254572 | 10/1999 |
| CA | 2 386 716 A1 | 11/2003 |
| EP | 0 005 129 B1 | 4/1981 |
| EP | 0 014 495 B1 | 1/1983 |
| EP | 1 230 237 B1 | 4/2004 |
| EP | 1 375 497 B1 | 9/2006 |
| WO | WO 92/08716 | 5/1992 |
| WO | WO 94/27988 A1 | 12/1994 |
| WO | WO 95/01977 A1 | 1/1995 |
| WO | WO 9602535 A1 | 2/1996 |
| WO | WO 96/17077 A1 | 6/1996 |
| WO | WO 97/02261 A1 | 1/1997 |
| WO | WO 97/41114 | 11/1997 |
| WO | WO 98/54171 | 12/1998 |
| WO | WO 01/36409 A1 | 5/2001 |
| WO | WO 03/008406 A1 | 1/2003 |
| WO | WO 03/051867 A1 | 6/2003 |
| WO | WO 2004/020436 A1 | 3/2004 |
| WO | WO 2004/046134 A2 | 6/2004 |

*Primary Examiner* — Patricia Morris
(74) *Attorney, Agent, or Firm* — Arent Fox LLP (57) ABSTRACT

The present invention relates to a process for removing an organic solvent from a salt of omeprazole, in particular a magnesium salt of omeprazole, a composition comprising a salt of omeprazole, in particular a magnesium salt of omeprazole obtainable by such a process, and pharmaceutical compositions comprising said composition or a salt of omeprazole, in particular a magnesium salt of omeprazole, in particular where omeprazole is S-omeprazole.

23 Claims, 2 Drawing Sheets

PROCESS FOR SOLVENT REMOVAL FROM OMEPRAZOLE SALTS

This application is the National Stage of International Application No. PCT/EP2008/050198, filed on Jan. 9, 2008, which claims benefit under 35 U.S.C. 119(a)-(d) or (f) or 365(b) of foreign applications EP 07100738.9, filed on Jan. 18, 2007, the contents of both are incorporated herein by reference in their entirety.

FIELD OF THE INVENTION

The present invention relates in general to the field of pharmaceutical compositions and in particular to the preparation of a salt of omeprazole, in particular a magnesium salt of omeprazole, which may be used in a pharmaceutical composition.

BACKGROUND OF THE INVENTION

The compound known under the generic name omeprazole is disclosed in EP 0 005 129.

Omeprazole is useful for inhibiting gastric acid secretion and has gastric mucosa protective activity in mammals and man. Omeprazole may be used for prevention and treatment of gastric acid related disorders and gastrointestinal inflammatory diseases in mammals and man, including for example gastritis, gastric ulcer and duodenal ulcer.

S-omeprazole magnesium, the generic name for magnesium bis(5-methoxy-2-[(S)-[(4-methoxy-3,5-dimethyl-2-pyridinyl)methyl]sulfinyl]-1H-benzimidazole), is a well-known gastric proton-pump inhibitor and has been commercially available from AstraZeneca under the brand name NEXIUM since 2001.

Certain salts of omeprazole are disclosed in EP 0 124 495. Canadian patent 2166794 disclosed a form of magnesium omeprazole dihydrate, which has a higher degree of crystallinity. This form has a methanol content of less than 0.1%.

Canadian patent application No. 2254572 discloses a process for the production of magnesium omeprazole crystalline dihydrate.

WO 97/41114 describes a procedure for preparing omeprazole magnesium and S-omeprazole magnesium with a low content of inorganic impurities.

EP 1 230 237 describes a procedure of removing residual solvents in omeprazole magnesium and EP 1 375 497 a procedure of removing residual solvents in S-omeprazole magnesium by flash evaporation but the products have unrepeatable low crystallinity between amorphous and a degree of crystallinity around 25% and still contain various amounts of residual solvents.

One enantiomer of omeprazole was prepared by separation of diastereoisomeric mixtures of derivatized omeprazole with further conversion to an enantiomer isolated as a syrupous substance in WO 92/08716.

A more convenient procedure for preparation of single isomer was done by chiral oxidation of a starting sulphide by cumene peroxide in the presence of titanium catalyst, diethyl tartrate and a base. The process is disclosed in WO 96/02535. The enantioselectivity of the foregoing transformation was high but there was still a need for removing residual R-enantiomer and overoxidation products like sulfones.

WO 97/02261 describes a method of further enrichment of S-enantiomer of omeprazole from already partially enriched mixtures by precipitating the racemate in selected solvents.

WO 96/17077 describes enzymatic enantioresolution of omeprazole and an analytical HPLC procedure of enantiomer determination.

WO 03/008406 describes a procedure of removing overoxidation products from S-enantiomer of omeprazole by extraction of S-enantiomer of omeprazole with water solution having selected pH values.

WO 94/27988 describes a solid form of S-omeprazole magnesium.

WO 95/01977 describes solid omeprazole magnesium with a degree of crystallinity over 70%.

WO 98/54171 describes a magnesium salt of S-omeprazole trihydrate characterized by being highly crystalline and stable. It discloses also polymorphic forms (A and B) of S-omeprazole magnesium salt dihydrate and processes for their preparation using S-omeprazole potassium salt as an intermediate.

WO 04/020436 discloses amorphous S-omeprazole magnesium salt in a hydrate form.

WO 04/046134 describes a crystalline S-omeprazole magnesium salt trihydrate form II wherein the term trihydrate is used to define a crystalline material in which water molecules are bound in the crystalline lattice.

WO 03/051867 describes separating omeprazole enantiomers by using simulated moving bed chromatography. Separation requires using technologically demanding procedures of chiral column chromatography to provide enantioresolution of 2-pyridinylmethylsulfinyl-1H-benzimidazoles.

In light of the foregoing, the object of the present invention was to produce a salt of omeprazole or its S-enantiomer that has acceptably low levels of organic solvent and can be produced by a simple process.

SUMMARY OF THE INVENTION

In general, the present invention is directed to a process for preparing a salt of omeprazole, in particular a magnesium salt of omeprazole.

In one aspect, the present invention provides a process for removing an organic solvent from a salt of omeprazole, comprising the step of
  (i) treating a salt of omeprazole containing at least one organic solvent with a gas comprising water vapors.

Preferably, the salt of omeprazole is a magnesium salt of omeprazole.

According to another embodiment, the present invention provides a process for removing an organic solvent from a magnesium salt of omeprazole as described above, wherein the magnesium salt of omeprazole containing at least one organic solvent is obtained by a process comprising the steps:
  (a) reacting omeprazole with a magnesium source in a solution of an organic solvent,
  (b) partly removing said organic solvent,
  (c) isolating a magnesium salt of omeprazole containing up to 5 wt.-% of said organic solvent.

Step (b) may for certain embodiments be optional.

The present invention also provides a process for removing an organic solvent from a salt of omeprazole, in particular a magnesium salt of omeprazole, as described above, wherein the organic solvent is a C1 to C4 alcohol or acetone, preferably methanol. The magnesium source preferably is a magnesium alcoholate of a C1 to C4 alcohol.

The present invention also provides a process for removing an organic solvent from a salt of omeprazole, in particular a magnesium salt of omeprazole as described above, wherein the salt of omeprazole, in particular the magnesium salt of omeprazole, contains more than 95% of the respective salt of omeprazole and less than 5% of omeprazole. The salt of omeprazole, in particular the magnesium salt of omeprazole, preferably is a solid salt of omeprazole, in particular a solid magnesium salt of omeprazole. In particular, the solid salt of omeprazole is crystalline or amorphous. It can be also in hydrated form, in particular dihydrate or trihydrate. In particular omeprazole is S-omeprazole.

According to one embodiment, the present invention provides a process for removing an organic solvent from a salt of omeprazole as described above, wherein the gas comprising water vapors is air or nitrogen comprising water vapors, preferably air or nitrogen saturated with water. Step (i) is preferably performed at room temperature.

The present invention further provides a process for removing an organic solvent from a salt of omeprazole as described above, wherein step (i) comprises blowing a gas comprising water vapors through the salt of omeprazole containing at least one organic solvent. Preferably, the gas is a gas stream.

According to another embodiment, the present invention provides for a process for improving the degree of crystallinity of a solid salt of omeprazole by
(i) treating a salt of omeprazole containing at least one organic solvent with a gas comprising water vapors.

Preferably, the degree of crystallinity is improved from below 25% to about 50% or more, more preferably, the degree of crystallinity is improved from below 30 to 50% to about 60 to 75%.

According to another embodiment, the present invention also provides a composition comprising a salt of omeprazole, in particular a magnesium salt of omeprazole obtainable according to a process of the present invention, preferably a composition, wherein the salt of omeprazole comprises less than 1 wt.-% of an organic solvent. Preferably, omeprazole is S-omeprazole. The organic solvent preferably is a C1 to C4 alcohol or acetone, more preferably methanol.

Furthermore, the present invention provides the use of a gas comprising water vapors for removing an organic solvent from a salt of omeprazole, in particular from a magnesium salt of omeprazole.

The present invention also provides a method of treating a gastrointestinal inflammatory disease or condition comprising orally administering to a patient in need of such treating a therapeutically effective amount of the composition according to the invention or a salt of omeprazole, in particular a magnesium salt of omeprazole, obtainable according to a process as described above and at least one pharmaceutically acceptable excipient.

Additionally, the present invention provides a pharmaceutical composition comprising the composition according to the invention or a salt of omeprazole, in particular a magnesium salt of omeprazole, obtainable according to a process as described above and at least one pharmaceutically acceptable excipient.

Finally, the present invention provides the use of a therapeutically effective amount of the composition according to the invention or a salt of omeprazole, in particular a magnesium salt of omeprazole, obtainable according to a process as described above and at least one pharmaceutically acceptable excipient for the preparation of a medicament for treating a gastrointestinal inflammatory disease or condition, preferably wherein said medicament is to be administered to a patient in need thereof.

Term about in this specification if not explicitly defined otherwise is meant to be within ±10% of the indicated value or, when expressed in % of purity or e.e. within 10% relative to (100−indicated values) and may in the strictest embodiment be omitted.

DESCRIPTION OF THE INVENTION

The present invention relates in general to the field of pharmaceutical compositions and in particular to the preparation of a salt of omeprazole, in particular a magnesium salt of omeprazole, which may be used in a pharmaceutical composition. The term omeprazole may encompass each specific enantiomer in the context of the present invention.

The present invention provides a process for removing an organic solvent from a salt of omeprazole, comprising the step of
(i) treating a salt of omeprazole containing at least one organic solvent with a gas comprising water vapors.

A salt of omeprazole can be any pharmaceutically acceptable salt of omeprazole in the context of the present invention. Suitable salts are any pharmaceutically acceptable salts of omeprazole known to the person skilled in the art, e.g. a salt of magnesium, calcium, sodium, potassium or the like. Preferably, the salt of omeprazole is a magnesium salt of omeprazole.

Therefore, the present invention according to another embodiment provides a process for removing an organic solvent from a magnesium salt of omeprazole, comprising the step of
(i) treating a magnesium salt of omeprazole containing at least one organic solvent with a gas comprising water vapors.

The term "treating" in the context of the present invention is to be understood as bringing into contact, in particular blowing through. Step (i) is also referred to as "drying" in the context of the present invention. A "magnesium salt of omeprazole" is also referred to as "magnesium omeprazole" or "omeprazole magnesium" in the context of the present invention.

In the following, as far as specific reference is made to a magnesium salt of omeprazole, this disclosure is also applicable to other salts of omeprazole. Even though the disclosure of the present invention focuses on salts of omeprazole, the process of the present invention can be applied for the removing an organic solvent from omeprazole as such in the same manner as discloses. The person skilled in the art will adjust the process according to the present invention where necessary for that application.

The process of the present invention surprisingly allows to reduce the amount of organic solvent in a salt of omeprazole, in particular a magnesium salt of omeprazole. It has been found that the amount of solvent which can remain in a salt of omeprazole, in particular a magnesium salt of omeprazole, can be significantly reduced by treating the salt of omeprazole, in particular the magnesium salt of omeprazole, containing at least one organic solvent with a gas comprising water vapors.

The degree of crystallinity (e.g. amorphous or crystalline) remains substantially unchanged if a salt, in particular a magnesium salt of an enantiomer of omeprazole is subjected to the above described treatment comprising step (i), while the degree of crystallinity is improved if an omeprazole racemate is subjected to the above described treatment according to the present invention. Thus, treating of an amorphous salt, in particular a magnesium salt of an omeprazole racemate yields crystalline dihydrate.

The process of the invention can be easily combined with known processes to prepare a salt of omeprazole, in particular a magnesium salt of omeprazole, which may contain an unsuitably high amount of an organic solvent for certain applications. In contrary to prior art procedures of removal of solvents from omeprazole salts this process is surprisingly applicable on racemic salts of omeprazole, in particular racemic magnesium salts of omeprazole as well as on salts of S-omeprazole, in particular S-omeprazole magnesium, and is efficient if said products are in amorphous or in highly crystalline state depending on preparation conditions.

According to the present invention, the salt of omeprazole, in particular the magnesium salt of omeprazole, can contain up to 10 wt.-% of an organic solvent, in particular up to 5 wt.-%, preferably up to 3 wt.-% or up to 2 wt.-%, in each case based on the amount of the salt of omeprazole.

The salt of omeprazole can be prepared according to any suitable process known, in particular by reacting omeprazole with a suitable compound, such as hydroxides, inorganic or organic salts. In particular, the magnesium salt of omeprazole can be prepared according to any suitable process known, in particular by reacting omeprazole with a suitable magnesium source.

Therefore, according to one embodiment, the present invention provides a process for removing an organic solvent from a magnesium salt of omeprazole as described above, wherein the magnesium salt of omeprazole containing at least one organic solvent is obtained by a process comprising the steps:
(a) reacting omeprazole with a magnesium source in a solution of an organic solvent,
(b) partly removing said organic solvent,
(c) isolating a magnesium salt of omeprazole containing up to 5 wt.-% of said organic solvent.

Steps (a), (b), and (c) can be performed according to general procedures known to the person skilled in the art. Step (b) can for example comprise an evaporation and may in certain embodiments be optional. Step (c) can for example comprise a filtration.

Therefore, according to one embodiment, the present invention provides a process for removing an organic solvent from a magnesium salt of omeprazole as described above, wherein the magnesium salt of omeprazole containing at least one organic solvent is obtained by a process comprising the steps:
(a) reacting omeprazole with a magnesium source in a solution of an organic solvent,
(b) optionally removing said organic solvent,
(c) isolating a magnesium salt of omeprazole containing up to 5 wt.-% of said organic solvent.

Thus, the present invention provides a process for removing an organic solvent from a magnesium salt of omeprazole, comprising the steps:
(a) reacting omeprazole with a magnesium source in a solution of an organic solvent,
(b) partly removing said organic solvent,
(c) isolating a magnesium salt of omeprazole containing up to 5 wt.-% of said organic solvent,
(i) treating a magnesium salt of omeprazole containing at least one organic solvent with a gas comprising water vapors.

Step (b) may be optional in certain embodiments. Generally, other salts of omeprazole can be prepared in an analogous manner.

According to the present invention, the salt of omeprazole preferably contains more than 95% of the salt of omeprazole and less than 5% of omeprazole. Therefore, according to another embodiment, the present invention provides a process for removing an organic solvent from a salt of omeprazole as described above, wherein the salt of omeprazole contains more than 95% of the salt of omeprazole and less than 5% of omeprazole.

According to a preferred embodiment, the salt of omeprazole preferably contains more than 95% of omeprazole magnesium and less than 5% of omeprazole. Therefore, according to another embodiment, the present invention provides a process for removing an organic solvent from a magnesium salt of omeprazole as described above, wherein the salt of omeprazole contains more than 95% of omeprazole magnesium and less than 5% of omeprazole.

Preferably, the salt of omeprazole is a solid salt of omeprazole which can be crystalline or amorphous. It can be also in hydrated form, in particular dihydrate or trihydrate. In particular omeprazole is S-omeprazole. Therefore, according to one embodiment, the present invention provides a process for removing an organic solvent from a salt of omeprazole as described above, wherein the salt of omeprazole is a solid salt of omeprazole.

In particular, the salt of omeprazole is a solid magnesium salt of omeprazole which can be crystalline or amorphous.

According to one embodiment, the present invention provides a process, wherein the solid salt of omeprazole, in particular the solid magnesium salt of omeprazole, is crystalline. According to another embodiment, the present invention provides a process, wherein the solid salt of omeprazole, in particular the solid magnesium salt of omeprazole, is amorphous.

Preferably, if omeprazole is S-omeprazole the obtained solid is form B. Therefore, according to one embodiment, the present invention provides a process for removing an organic solvent from a salt of omeprazole as described above, wherein if omeprazole is S-omeprazole the obtained solid is form B.

The solid salt of omeprazole, in particular the solid magnesium salt of omeprazole, can have a crystallinity of more than 70%. According to the present invention, the solid salt of omeprazole, in particular the solid magnesium salt of omeprazole, can also have a crystallinity of less than 70%. Therefore, according to one embodiment, the present invention provides a process, wherein the solid salt of omeprazole has a crystallinity of more than 70%. According to another embodiment, the present invention provides a process, wherein the solid salt of omeprazole has a crystallinity of less than 70%, which can be measured as described in WO 95/01977.

Suitable magnesium sources for use in the present invention include magnesium hydroxide, magnesium inorganic salts such as magnesium sulphate, magnesium chloride, magnesium carbonate and magnesium nitrate; magnesium organic salts selected from a group consisting of magnesium 2-ethyl-hexanoate, magnesium citrate, magnesium stearate, magnesium ascorbate, magnesium acetate, magnesium alcoholate, and mixtures thereof. Preferably, the magnesium source is a magnesium alcoholate of a C1 to C4 alcohol, such as magnesium ethanolate or magnesium methanolate. More preferably, magnesium methanolate in a methanol solution is used as magnesium source.

According to one embodiment, the present invention provides a process for removing an organic solvent from a magnesium salt of omeprazole as described above, wherein the magnesium source is magnesium alcoholate of a C1 to C4 alcohol.

According to the present invention, the organic solvent can be any solvent which may remain in a salt of omeprazole, in particular in a magnesium salt of omeprazole, due to a preparation process and which can be removed by a treatment according to step (i). In particular, the organic solvent may be an ether, an alcohol, or a ketone, such as acetone, preferably a C1 to C4 alcohol, such as methanol or ethanol, more preferably methanol.

According to one embodiment, the present invention provides a process for removing an organic solvent from a salt of omeprazole, in particular from a magnesium salt of omeprazole, as described above, wherein the organic solvent is a C1 to C4 alcohol or acetone.

According to one embodiment, the present invention provides a process for removing an organic solvent from a salt of omeprazole, in particular a magnesium salt of omeprazole, as described above, wherein the C1 to C4 alcohol is methanol.

According to the present invention, the process can comprise further steps, for example purification steps or steps to reduce the amount of solvent in the magnesium salt between the steps, in particular between steps (c) and (i). For example, the process can comprise a further evaporation, for example a flash-evaporation between steps (c) and (i).

According to a preferred embodiment, omeprazole is S-omeprazole. Preferably, omeprazole is a mixture of S-omeprazole and R-omeprazole in e.e. of more than 90%, preferably more than 96%, more preferably more than 98%, most preferably more than 99.5%, according to the present invention.

According to the present invention, the salt of omeprazole, in particular the magnesium salt of omeprazole, is treated with a gas comprising water vapors according to step (i). This gas can be any suitable gas as long as it comprises water vapors and does not react with the salt of omeprazole. In particular, the gas can be oxygen, nitrogen, a nobel gas like argon, helium or neon, or mixtures of these. Preferably, the gas is nitrogen or air. The gas can comprise any suitable amount of water vapors. Preferably the gas is saturated with water.

According to one embodiment, the present invention provides a process for removing an organic solvent from a salt of omeprazole, in particular a magnesium salt of omeprazole, as described above, wherein the gas comprising water vapors is air or nitrogen comprising water vapors, preferably air or nitrogen saturated with water.

The treating according to step (i) is preferably carried out at a temperature of from about 10° C. to about 40° C., preferably at about room temperature. The time for treating the salt of omeprazole, in particular the magnesium salt of omeprazole, may range from about 1 hour to about 48 hours, preferably from about 5 hour to about 36 hours, most preferably from about 10 hour to about 24 hours, for example about 15 hours or about 20 hours.

The treating according to step (i) is carried out at atmospheric pressure or at a reduced pressure, preferably at a reduced pressure of from about 50 mbar to about 500 mbar.

According to one embodiment, the present invention provides a process for removing an organic solvent from a salt of omeprazole, in particular a magnesium salt of omeprazole, as described above, wherein step (i) is performed at room temperature.

According to one embodiment, the present invention provides a process for removing an organic solvent from a salt of omeprazole, in particular a magnesium salt of omeprazole, as described above, wherein step (i) comprises blowing a gas comprising water vapors through the salt of omeprazole, in particular through the magnesium salt of omeprazole, containing at least one organic solvent.

Preferably, the gas comprising water vapors is used in form of a gas stream comprising water vapors according to the present invention. Therefore, according to a further embodiment, the present invention provides a process for removing an organic solvent from a salt of omeprazole, in particular a magnesium salt of omeprazole, as described above, wherein the gas comprising water vapors is a gas stream comprising water vapors.

According to another embodiment, the present invention also provides the use of a gas comprising water vapors for removing an organic solvent from a salt of omeprazole. In particular, the present invention provides the use of a gas comprising water vapors for removing an organic solvent from a magnesium salt of omeprazole.

According to another embodiment, the present invention provides for a process for improving the degree of crystallinity of a solid salt of omeprazole by
(i) treating a salt of omeprazole containing at least one organic solvent with a gas comprising water vapors.

Preferably, the salt of omeprazole is a magnesium salt of omeprazole. Therefore, the present invention also provides a process for improving the degree of crystallinity of a solid magnesium salt of omeprazole by
(i) treating a magnesium salt of omeprazole containing at least one organic solvent with a gas comprising water vapors.

Preferably, the degree of crystallinity is improved from below 25% to about 50% or more, in particular to 50% or more, more preferably, the degree of crystallinity is improved from below 30 to 50% to about 60 to 75%, in particular to 60 to 75%.

Therefore, according to another embodiment, the present invention provides a process for improving the degree of crystallinity of a solid salt of omeprazole, in particular a solid magnesium salt of omeprazole, as disclosed above, wherein the degree of crystallinity is improved from below 25% to about 50% or more, preferably wherein the degree of crystallinity is improved from below 30 to 50% to about 60 to 75%.

According to another embodiment of the present invention, omeprazole is S-omeprazole. Therefore, the present invention also provides a process for improving the degree of crystallinity of a solid salt of omeprazole, in particular a solid magnesium salt of omeprazole, as disclosed above, wherein omeprazole is S-omeprazole.

The residual organic solvent content by weight of the salt of omeprazole obtained according to the present invention will be under 1 wt.-%, preferably under 0.99 wt.-%, more preferably under 0.98 wt.-%, for example under 0.95 wt.-%, under 0.90 wt.-%, under 0.85 wt.-%, under 0.80 wt.-%, under 0.75 wt.-%, under 0.70 wt.-%, under 0.65 wt.-%, under 0.60 wt.-%, under 0.55 wt.-%, under 0.50 wt.-%, under 0.45 wt.-%, under 0.40 wt.-%, under 0.35 wt.-%, under 0.30 wt.-%, or under 0.25 wt.-% based on the amount of the salt of omeprazole.

In particular, the residual organic solvent content by weight of the magnesium omeprazole obtained according to the present invention will be under 1 wt.-%, preferably under 0.99 wt.-%, more preferably under 0.98 wt.-%, for example under 0.95 wt.-%, under 0.90 wt.-%, under 0.85 wt.-%, under 0.80 wt.-%, under 0.75 wt.-%, under 0.70 wt.-%, under 0.65 wt.-%, under 0.60 wt.-%, under 0.55 wt.-%, under 0.50 wt.-%, under 0.45 wt.-%, under 0.40 wt.-%, under 0.35 wt.-%, under 0.30 wt.-%, or under 0.25 wt.-% based on the amount of the magnesium salt of omeprazole.

Salts of omeprazole, in particular magnesium salts of omeprazole, comprising less than 1 wt.-% of an organic solvent based on the amount of the salt of omeprazole are particularly useful because organic solvents generally are not allowed in pharmaceutical compositions in higher amounts.

Therefore, the present invention also provides a composition comprising a salt of omeprazole, in particular a magnesium salt of omeprazole, obtainable by a process according to the present invention. Therefore, the present invention also provides a composition comprising a salt of omeprazole, in particular a magnesium salt of omeprazole, obtainable by a process according to the above described embodiments of the present invention. The present invention provides a composition comprising a salt of omeprazole obtainable by a process for removing an organic solvent from a salt of omeprazole, comprising the step of
(i) treating a salt of omeprazole containing at least one organic solvent with a gas comprising water vapors.

The present invention also provides a composition comprising a magnesium salt of omeprazole obtainable by a process for removing an organic solvent from a magnesium salt of omeprazole, comprising the step of
(i) treating a magnesium salt of omeprazole containing at least one organic solvent with a gas comprising water vapors.

According to another embodiment, the present invention also provides a composition comprising a salt of omeprazole as described above, wherein the salt of omeprazole comprises less than 1 wt.-% of an organic solvent, preferably less than 0.99 wt.-%, more preferably less than 0.98 wt.-%, for example less than 0.95 wt.-%, less than 0.90 wt.-%, less than 0.85 wt.-%, less than 0.80 wt.-%, less than 0.75 wt.-%, less than 0.70 wt.-%, less than 0.65 wt.-%, less than 0.60 wt.-%, less than 0.55 wt.-%, less than 0.50 wt.-%, less than 0.45 wt.-%, less than 0.40 wt.-%, less than 0.35 wt.-%, less than 0.30 wt.-%, or less than 0.25 wt.-% based on the amount of the salt of omeprazole.

According to a preferred embodiment, the present invention also provides a composition comprising a magnesium salt of omeprazole, wherein the magnesium salt of omeprazole comprises less than 1 wt.-% of an organic solvent, preferably less than 0.99 wt.-%, more preferably less than 0.98 wt.-%, for example less than 0.95 wt.-%, less than 0.90 wt.-%, less than 0.85 wt.-%, less than 0.80 wt.-%, less than 0.75 wt.-%, less than 0.70 wt.-%, less than 0.65 wt.-%, less than 0.60 wt.-%, less than 0.55 wt.-%, less than 0.50 wt.-%, less than 0.45 wt.-%, less than 0.40 wt.-%, less than 0.35 wt.-%, less than 0.30 wt.-%, or less than 0.25 wt.-% based on the amount of the magnesium salt of omeprazole.

In view of the organic solvent, reference is made to the above disclosure.

Therefore, the present invention also provides a composition comprising a salt of omeprazole as described above, in particular a magnesium salt of omeprazole as described above, wherein the salt of omeprazole, in particular the magnesium salt of omeprazole, comprises less than 1 wt.-% of an organic solvent. According to a further embodiment, the present invention also provides a composition comprising a salt of omeprazole as described above, in particular a magnesium salt of omeprazole as described above, wherein the organic solvent is a C1 to C4 alcohol or acetone, preferably methanol.

According to one embodiment, the present invention provides a process for removing an organic solvent from a salt of omeprazole, in particular a magnesium salt of omeprazole, as described above, wherein omeprazole is S-omeprazole. In this case, a salt, in particular a magnesium salt of S-omeprazole is used in the process according to the present invention. In particular, amorphous or crystalline salts, in particular magnesium salts of S-omeprazole, or hydrates thereof can be used in the said process.

Therefore, the present invention also provides a composition comprising a salt of omeprazole as described above, in particular a magnesium salt of omeprazole as described above, wherein the salt of omeprazole comprises less than 1 wt.-% of an organic solvent as described above wherein omeprazole is S-omeprazole.

The S-omeprazole can be prepared according to any suitable process known and then be converted to the respective magnesium salt by:
(a') reacting S-omeprazole with a magnesium source in a solution of an organic solvent,
(b') optionally, partly removing said organic solvent,
(c') isolating a magnesium salt of S-omeprazole containing up to 5 wt.-% of said organic solvent.

Thus, the present invention provides a process for removing an organic solvent from a magnesium salt of S-omeprazole, comprising the steps:
(a') reacting S-omeprazole with a magnesium source in a solution of an organic solvent,
(b') optionally, partly removing said organic solvent,
(c') isolating a magnesium salt of S-omeprazole containing up to 5 wt.-% of said organic solvent,
(i') treating a magnesium salt of S-omeprazole containing at least one organic solvent with a gas comprising water vapors.

In a more specific embodiment the present invention provides a process for removing an organic solvent from a magnesium salt of S-omeprazole, comprising the steps:
(a') reacting S-omeprazole with a magnesium source in a solution of an organic solvent,
(b') optionally, partly removing said organic solvent,
(c') isolating an amorphous magnesium salt of S-omeprazole containing up to 5 wt.-% of said organic solvent,
(i') treating a magnesium salt of S-omeprazole containing at least one organic solvent with a gas comprising water vapors,
(e') optionally, redrying the product to reduce the water content.

In a preferred example of the embodiment the organic solvent is a C1-C4 alcohol preferably methanol.

In another more specific embodiment the present invention provides a process for removing an organic solvent from a magnesium salt of S-omeprazole, comprising the steps:
(a') reacting S-omeprazole with a magnesium source in a solution of an organic solvent,
(b') optionally, partly removing said organic solvent,
(c') optionally, adding a new solvent,
(d') isolating an crystalline magnesium salt of S-omeprazole containing up to 5 wt.-% of said organic solvent,
(i') treating a magnesium salt of S-omeprazole containing at least one organic solvent with a gas comprising water vapors.

In a preferred example of the embodiment the organic solvent is selected from ketones, preferably from acetone, and the crystalline form obtained is a dihydrate form B which is described in WO 98/54171.

It is possible to prepare S-omeprazole by a two-step process for the industrial preparation of S-omeprazole magnesium starting from racemic omeprazole. The process comprises at least a separation step carried out by chiral column chromatography to yield S-omeprazole, and a subsequent step of making a magnesium salt of the S-omeprazole by addition of a source of magnesium, such as magnesium methanolate solution, to a concentrated column eluate, and precipitation of the salt in an organic solvent.

In more detail, a suitable process is shown below as Scheme 1. According to Scheme 1, preparation of S-omeprazole magnesium from omeprazole may be accomplished by:
(a) enantioresolution of omeprazole enantiomers by chiral column chromatography using a coated polysaccharide on silica support as a chiral stationary phase and using an alcohol as a mobile phase; and (b) concentration of the column eluates, followed by addition of magnesium methanolate solution as a source of magnesium to the concentrate of S-omeprazole, and final precipitation of S-omeprazole magnesium in an organic solvent and isolation of the separated solid mass by filtration.

Scheme I

Using such procedure, S-omeprazole magnesium having an optical purity of at least 85% e.e., preferably at least 89% e.e. may be obtained. In particular, the optical purity of the final S-omeprazole magnesium may range from about 85% e.e. to about 99% e.e.

According to the present invention, omeprazole preferably is a mixture of S-omeprazole and R-omeprazole in e.e. of more than 90%, preferably more than 96%, more preferably more than 98%, most preferably more than 99.5%.

Preferably, the collected eluates of S-omeprazole from the enantioresolution are concentrated to a smaller volume by partial distillation of the mobile phase solvent which is preferably an alcohol such as methanol. A magnesium source is then added to the concentrate of neutral S-omeprazole to produce the S-omeprazole magnesium salt. Suitable magnesium sources for use in the present invention include magnesium hydroxide, magnesium inorganic salts such as magnesium sulphate, magnesium chloride, magnesium carbonate and magnesium nitrate; magnesium organic salts selected from a group consisting of magnesium 2-ethyl-hexanoate, magnesium citrate, magnesium stearate, magnesium ascorbate, magnesium acetate, magnesium alcoholate, and mixtures thereof. Preferably, the magnesium source is a magnesium alcoholate, such as magnesium ethanolate or magnesium methanolate. More preferably, magnesium methanolate in a methanol solution is used as magnesium source.

After the reaction with the magnesium source is substantially completed, solid inorganic magnesium salts residues are removed. Optionally, a small amount of water (up to 1% (V/V) calculated on the volume (V) of reaction mixture) is added to the reaction mixture in order to precipitate surplus amount of magnesium source. Preferably, the obtained reaction mixture containing S-omeprazole magnesium is filtered through a layer of diatomite filter medium (Celite®). In the next step the S-omeprazole magnesium is precipitated from the reaction mixture. Depending on the preparation conditions either amorphous or crystalline S-omeprazole magnesium salt is obtained.

According to the first embodiment, the filtrate of the reaction mixture is then poured into a substantially nonpolar organic solvent such as an ether solvent in order to precipitate the S-omeprazole magnesium. Suitable ether solvents for use in the present invention may be selected from the group consisting of diethyl ether, methyl t-butyl ether, diisopropyl ether, and mixtures of one or more thereof. Most preferably, diethyl ether is used for precipitation of S-omeprazole magnesium. The temperature of precipitation medium may be in the range of from about 30° C. to about −30° C., preferably from about 20° C. to about −10° C.

By implementing the step (i) of this invention the formed S-omeprazole magnesium salt comprises less than 1 wt.-% of an organic solvent, preferably less than 0.99 wt.-%, more preferably less than 0.98 wt.-%, for example less than 0.95 wt.-%, less than 0.90 wt.-%, less than 0.85 wt.-%, less than 0.80 wt.-%, less than 0.75 wt.-%, less than 0.70 wt.-%, less than 0.65 wt.-%, less than 0.60 wt.-%, less than 0.55 wt.-%, less than 0.50 wt.-%, less than 0.45 wt.-%, less than 0.40 wt.-%, less than 0.35 wt.-%, less than 0.30 wt.-%, or less than 0.25 wt.-% based on the amount of the magnesium salt of S-omeprazole. According to X-ray powder diffraction analysis the S-omeprazole magnesium prepared according to this process is obtained in an amorphous form. The diffractogram of a respective sample is shown on the FIG. 1.

Optionally the amorphous solvent pure S-omeprazole magnesium can be additionally dried in vacuo bellow 40° C. to obtain a product having a water content bellow about 4.8 wt-%, preferably below about 3.2 wt-%, and most preferably below about 2.5 wt-%.

According to the second embodiment, organic solvent is partly removed from the filtrate of the reaction mixture forming a S-omeprazole magnesium solution having concentration 10 to 70 wt.-%, preferably 30 to 50 wt.-%. Addition of a mixture of a second organic solvent and water to the said solution results in formation of a solid S-omeprazole magnesium salt. Optionally, the reaction mixture can be seeded with S-omeprazole magnesium salt crystals. The second organic solvent used for precipitation of the product is selected from a group of ketones or alcohols. From alcohols precipitates an amorphous solid, while ketones facilitate formation of crystalline form B. Thus in this second aspect acetone is most preferred. The aqueous second organic solvent comprises 2 to 20% (V/V) of water, more preferably 5 to 10% (V/V) of water. The temperature of precipitation medium may be in the range of from about 50° C. to about −10° C., preferably from about 25° C. to about 0° C. The solid product is separated by filtration or centrifugation and optionally washed with a small amount of the aqueous organic solvent.

The isolated solid product is in the next step subjected to the step (i) disclosed in this invention, thus the magnesium salt of S-omeprazole containing up to 10 wt.-% of organic solvent is treated with a gas comprising water vapors at reduced pressure. The step is also referred to as drying and is performed by gas steam of either air or nitrogen saturated with water at the temperatures from about 50° C. to about 20° C., at reduced pressure, preferably at pressure between 500 and 50 mbar.

The obtained S-omeprazole magnesium salt is having a water content between 4.5 wt.-% and 6.7 wt.-%, comprising less than 1 wt.-% of an organic solvent, preferably less than 0.99 wt.-%, more preferably less than 0.98 wt.-%, for example less than 0.95 wt.-%, less than 0.90 wt.-%, less than 0.85 wt.-%, less than 0.80 wt.-%, less than 0.75 wt.-%, less than 0.70 wt.-%, less than 0.65 wt.-%, less than 0.60 wt.-%, less than 0.55 wt.-%, less than 0.50 wt.-%, less than 0.45 wt.-%, less than 0.40 wt.-%, less than 0.35 wt.-%, less than 0.30 wt.-%, or less than 0.25 wt.-% based on the amount of the magnesium salt of S-omeprazole. X-ray powder diffraction analysis of a respective sample the S-omeprazole magnesium prepared according to the process of this embodiment gave the diffractogram depicted in the FIG. 2. The diffraction pattern corresponds to the diffraction pattern of S-omeprazole magnesium dihydrate form B as described in WO 98/54171.

S-omeprazole magnesium prepared by the processes described in the above embodiments exhibit improved characteristics which are believed to be due to low content or residual solvents and highly efficient enantiopurification.

The salt of omeprazole or S-omeprazole, preferably the magnesium salt of omeprazole or S-omeprazole, of the present invention or the salt of omeprazole or S-omeprazole, preferably the magnesium salt of omeprazole or S-omeprazole, obtainable by a process according to the present invention can be further processed into pharmaceutical compositions such as, for example, tablets for oral administration. The tablets will preferably be enteric coated to protect the salt of omeprazole, in particular the magnesium omeprazole, from the effects of gastric acid.

According to another embodiment, the present invention also provides a method of treating a gastrointestinal inflammatory disease or condition comprising orally administering to a patient in need of such treating a therapeutically effective amount of the composition according to the present invention or a salt of omeprazole or S-omeprazole, preferably the magnesium salt of omeprazole or S-omeprazole, obtainable according to a process as described above and at least one pharmaceutically acceptable excipient.

The salt of omeprazole or S-omeprazole, preferably the magnesium salt of omeprazole or S-omeprazole, of the present invention or the salt of omeprazole or S-omeprazole, preferably the magnesium salt of omeprazole or S-omeprazole, obtainable by a process according to the present invention may be used for inhibiting gastric acid secretion in mammals and man. In a more general sense, the compounds of the invention may be used for the treatment of gastric acid-related diseases and gastrointestinal inflammatory diseases in mammals and man, such as gastric ulcer, duodenal ulcer, reflux esophagitis and gastritis. Furthermore, the compounds may be used for treatment of other gastrointestinal disorders where gastric antisecretory effect is desirable, e.g., in patients on NSAID therapy, in patients with gastrinomas, and in patients with acute upper gastrointestinal bleeding. They may also be used in patients in intensive care situations, and pre- and post-operatively to prevent acid aspiration and stress ulceration.

The salt of omeprazole or S-omeprazole, preferably the magnesium salt of omeprazole or S-omeprazole, of the present invention or the salt of omeprazole or S-omeprazole, preferably the magnesium salt of omeprazole or S-omeprazole, obtainable by a process according to the present invention may also be used for treatment or prophylaxis of inflammatory conditions in mammals, including man, especially those involving lysozymal enzymes. Conditions that may be specifically mentioned for treatment are rheumatoid arthritis and gout. The salt of omeprazole or S-omeprazole, preferably the magnesium salt of omeprazole or S-omeprazole, of the present invention or the salt of omeprazole or S-omeprazole, preferably the magnesium salt of omeprazole or S-omeprazole, obtainable by a process according to the present invention may also be useful in the treatment of psoriasis, as well as in the treatment of Helicobacter infections.

According to another embodiment, the present invention also provides a pharmaceutical composition comprising the composition according to the present invention or a salt of omeprazole or S-omeprazole, preferably the magnesium salt of omeprazole or S-omeprazole, obtainable according to a process as described above and at least one pharmaceutically acceptable excipient.

Any suitable form of administration may be employed providing the patient with an effective dosage of the salt of omeprazole or S-omeprazole, preferably the magnesium salt of omeprazole or S-omeprazole, according to the invention. For example, peroral or parental formulations and the like may be employed. Dosage forms include capsules, tablets, dispersions, suspensions and the like.

For the preparation of pharmaceutical compositions in the form of dosage units for oral administration such as, for example, tablets, the salt of omeprazole or S-omeprazole, preferably the magnesium salt of omeprazole or S-omeprazole, of the present invention or the salt of omeprazole or S-omeprazole, preferably the magnesium salt of omeprazole or S-omeprazole, obtainable by a process according to the present invention may be combined with one or more pharmaceutically acceptable excipients including a solid, pulverulent carrier, such as lactose, saccharose, sorbitol, mannitol, starch, amylopectin, cellulose derivatives or gelatin, as well as an antifriction agent such as magnesium stearate, calcium stearate and polyethyleneglycol waxes. The mixture is then pressed into tablets. If coated tablets are desired, the above-prepared core may be coated with a concentrated solution of sugar, which may contain gum arabic, gelatin, talc, titanium dioxide, or with a pharmaceutically acceptable lacquer dissolved in volatile organic solvent or mixture of solvents. To this coating various pharmaceutically acceptable dyes may be added in order to distinguish among tablets with different amounts of active compound present. Soft gelatin capsules may be prepared which contain a mixture of the salt of omeprazole or S-omeprazole, preferably the magnesium salt of omeprazole or S-omeprazole, of the present invention or the salt of omeprazole or S-omeprazole, preferably the magnesium salt of omeprazole or S-omeprazole, obtainable by a process according to the present invention and vegetable oil. Hard gelatin capsules may contain granules of the active compound in combination with a solid, pulverulent carrier, such as lactose, saccharose, sorbitol, mannitol, potato starch, corn starch, amylopectin, cellulose derivatives, gelatin, and mixtures thereof.

The invention also provides the use of the salt of omeprazole or S-omeprazole, preferably the magnesium salt of omeprazole or S-omeprazole, of the invention in the manufacture of a medicament for the use in the treatment of a gastric-acid related condition or a method of treating a gastric-acid related condition which method comprises administering to subjects suffering from said condition a therapeutically effective amount of the salt of omeprazole or S-omeprazole, preferably the magnesium salt of omeprazole or S-omeprazole, according to the invention.

The invention also provides the use of a therapeutically effective amount of the composition according to the present invention or a salt of omeprazole or S-omeprazole, preferably the magnesium salt of omeprazole or S-omeprazole, obtainable according to a process as described above and at least one pharmaceutically acceptable excipient for the preparation of a medicament for treating a gastrointestinal inflammatory disease or condition, preferably wherein said medicament is to be administered to a patient in need thereof.

Combination preparations comprising the salt of omeprazole or S-omeprazole, preferably the magnesium salt of omeprazole or S-omeprazole, according to the present invention and other active ingredients may also be used. Examples of such active ingredients include, but are not limited to antibacterial compounds, non-steroidal anti-inflammatory agents, antacid agents, alginates and prokinetic agents.

The following examples illustrate the process of the present invention and are not intended to limit the scope of the invention set forth in the claims appended thereto.

EXAMPLES

Example 1

Omeprazole (10 g) is suspended in 33 mL of methanol. 17.4 mL of 8.8% solution of magnesium methanolate in methanol (1.25 g Mg(OMe)$_2$) is added to the omeprazole suspension. The reaction mixture is stirred for half an hour at room temperature. After filtration through a layer of diatomite filter medium (Celite®) it is slowly poured into 0.5 L of cold diethyl ether (−10° C.) under vigorous stirring. The formed suspension is kept at −10° C. for an hour. After filtration and washing with 100 mL of diethyl ether the wet filter cake is dried for 24 hours at reduced pressure (200 mbar) in the presence of air saturated with water at 40° C. 8.23 g of crystalline omeprazole magnesium (omeprazole magnesium dihydrate) containing less than 0.5 wt.-% of residual solvents (methanol, diethylether) is obtained.

Example 2

Racemic mixture of omeprazole is resolved and separated into S- and R-enantiomer using chiral column chromatography. Omeprazole is dissolved in methanol and diluted to a concentration of about 22-25 g/L. About 0.01% (V/V) of diethylamine is also added to the solution. The chromatographic separation is carried out under the following conditions:
Stationary phase: CHIRALPAK AD, 20 µm particle size
Column length: 250-350 mm
Column diameter: 5 cm
Mobile phase: methanol
Loading: $m_{LOAD}/S_{COLUMN}$=175-220 mg/cm$^2$, Linear velocity=3.8-4.2 cm/min.
Temperature: room temperature
Linear velocity during S-enantiomer elution: 5.7-6.2 cm/min.
Linear velocity during R-enantiomer elution: 9.0-11.8 cm/min.
UV detector: 325 nm
Run time: 22-26 min Combined fractions of S-omeprazole (2130 mL of a solution containing 11.13 g of S-omeprazole) produced by chiral column chromatography are concentrated approximately 100-fold by evaporation to produce a solution containing about 500 g/L of S-omeprazole in methanol. A 6 wt.-% solution of magnesium methanolate in methanol is prepared by reacting 0.398 g of magnesium turnings in 29 mL of methanol with a catalytic amount of dichloromethane. 29 mL of the solution of magnesium methanolate (1.41 g Mg(OMe)$_2$) is added to the concentrated solution of S-omeprazole. The reaction mixture is stirred for 0.5 hour at room temperature under inert atmosphere. Then, it is slowly poured into 0.55 L of diethyl ether being vigorously stirred. The suspension is cooled −10° C. and kept at this temperature for 1 hour to complete precipitation the S-omeprazole magnesium product. The product is filtered off and washed with 50 mL of diethyl ether. The product is dried overnight at 40° C. in vacuum to reduce residual methanol content to approximately 4 wt.-%. Further, a stream of nitrogen saturated with water at room temperature is blown through the filter cake for 5 h. Then, the product is re-dried for 24 h at 40° C. in vacuum. Amorphous S-omeprazole magnesium with residual methanol content below 0.5 wt.-% (determined by GC Headspace method) is obtained.

Example 3

7.2 kg of omeprazole is resolved and separated into S- and R-enantiomers using chiral column chromatography. Omeprazole is dissolved in methanol and diluted to a concentration of about 22-25 g/L. About 0.01% (V/V) of diethylamine is also added to the solution. The chromatographic separation is carried out under the analogous conditions as described in Example 2 using a column of length 300 mm and of diameter 15 cm.

Figure 1:
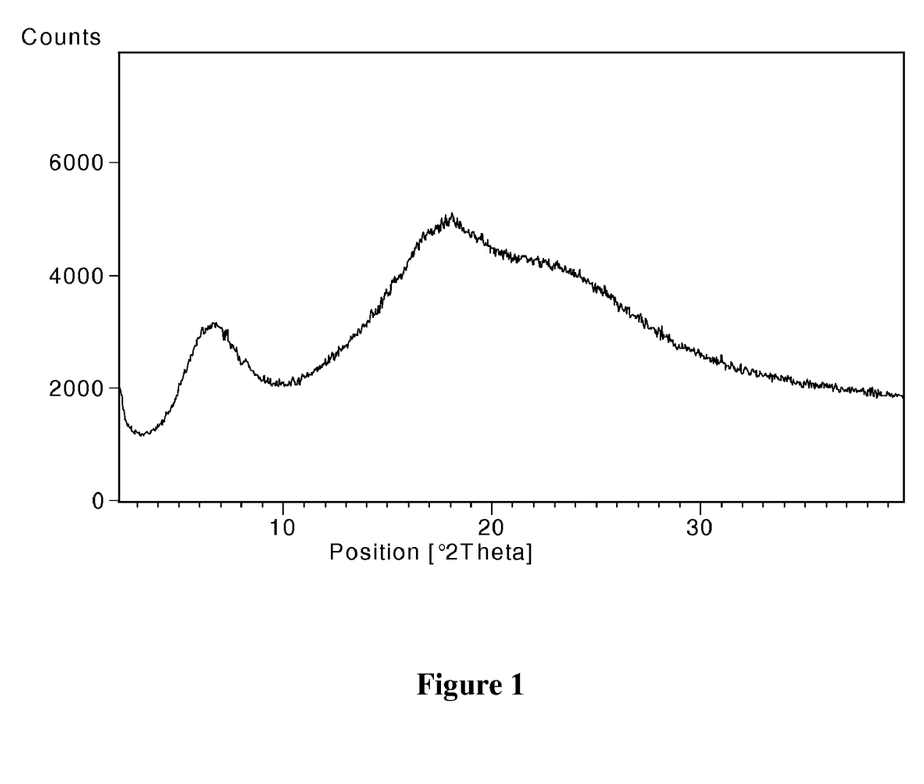
FIG. 1 shows the XRD diffractogram of the amorphous S-omeprazole magnesium obtained according to example 3.

Combined fractions of S-omeprazole produced by chiral column chromatography are concentrated by evaporation at reduced pressure to produce a solution containing about 600 g/L of S-omeprazole in methanol. 5.33 kg of 7.6 wt.-% solution of magnesium methanolate in methanol is added to the concentrated solution of S-omeprazole. The reaction mixture is stirred for 0.5 hour at 20° C. under N$_2$ atmosphere. Then, the reaction mixture is filtered through a layer of diatomite filter medium (Celite®) and slowly pumped into a reactor containing 153 kg of diethyl ether cooled to −10° C. The precipitation medium is vigorously stirred during the addition of the S-omeprazole magnesium solution. The formed suspension is stirred for another hour at −10° C. The product is filtered off and washed with 10 kg of diethyl ether. 7 kg of wet S-omeprazole magnesium (containing 6-8 wt.-% of methanol and 35-60 wt.-% of diethyl ether) is dried for 16 hours at 40° C. in vacuum in order to reduce residual solvents content to approximately 2.5 wt.-% of methanol and less than 100 ppm (w/w) of diethyl ether. The product contains 2.2 wt.-% of water. Further, nitrogen saturated with water at room temperature is blown through the filter cake until water content in the product is increased to 6-7 wt.-%. The residual methanol content is decreased below 0.5 wt.-%. Finally, S-omeprazole magnesium is dried for some additional time (30 hours) in vacuum at 40° C. yielding 3.34 kg of amorphous S-omeprazole magnesium (92.4% e.e. determined by chiral HPLC, 99.81% purity determined by HPLC, 4.0% of water content determined by Karl-Fisher, 3.8% of Mg determined by atomic absorption spectroscopy (AAS), assay of $C_{34}H_{36}N_6O_6S_2Mg$ 99.3% determined by HPLC, residual solvents content 2471 ppm (w/w) MeOH, <100 ppm (w/w) diethyl ether determined by GC Headspace method). The XRD diffractogram of the amorphous S-omeprazole magnesium is shown in FIG. 1.

Example 4

Figure 2:
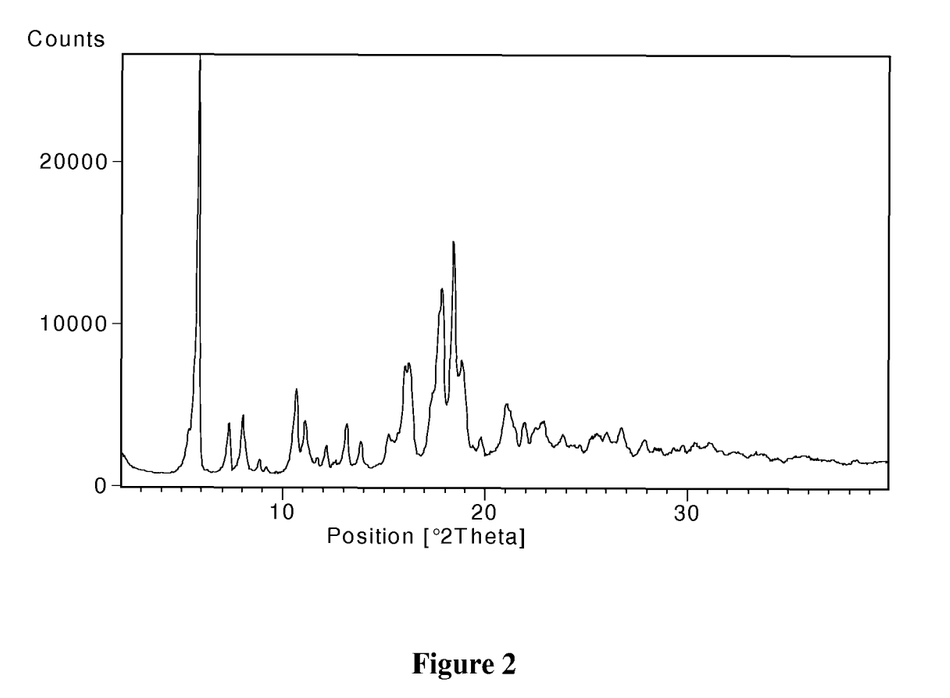
FIG. 2 shows the XRD diffractogram of S-omeprazole magnesium dihydrate form B obtained according to example 4.

A stoichiometric amount of 7.6 wt.-% methanolic solution of magnesium methanolate (18.1 mL) is added to the solution of 9.0 g of S-omeprazole (99.28% e.e.) in 100 mL of methanol. The solution of S-omeprazole is prepared by concentration of the combined fractions produced by chiral column chromatography under the chromatographic conditions presented in Example 2. The obtained reaction mixture is stirred at room temperature for 1 hour allowing to form S-omeprazole magnesium salt in the meantime. After addition of 0.4 mL of water the reaction mixture is further stirred for 30 min. The formed inorganic solid salt is separated from the liquid by filtration through a layer of diatomite filter medium (Celite®). The volume of filtrate is then reduced by evaporation of methanol forming an S-omeprazole magnesium solution with concentration 40-45 wt.-%. A mixture of 51 mL of acetone and 2.9 mL of water is added to the concentrate. The mixture is seeded with a 0.05 g of S-omeprazole magnesium dihydrate form B. After a few minutes a precipitate is formed and the suspension is stirred for 4 hours. The product is filtered off, washed twice with 10 mL of a mixture of acetone and methanol (4/1 (V/V)). The wet filter cake is dried for 20 hours at reduced pressure (200 mbar) in the presence of air saturated with water at 35° C. 8.00 g of S-omeprazole magnesium dihydrate form B is obtained (99.84% e.e. determined by chiral HPLC, 100% purity determined by HPLC, 5.31% of water content determined by Karl-Fisher, 3.6% of Mg determined by complexometric titration, assay of $C_{34}H_{36}N_6O_6S_2Mg$ 100.1% determined by HPLC, residual solvents content 1106 ppm (w/w) MeOH, 4439 ppm (w/w) acetone determined by GC Headspace method). The XRD diffractogram of the sample of the product is shown in FIG. 2.

The invention claimed is:

1. A process for removing an organic solvent from a salt of omeprazole, comprising the step of
   (i) treating a salt of omeprazole containing at least one organic solvent with a gas comprising water vapors.

2. The process of claim 1, wherein the salt of omeprazole is a magnesium salt of omeprazole.

3. The process of claim 2, wherein the magnesium salt of omeprazole containing at least one organic solvent is obtained by a process comprising the steps:
   (a) reacting omeprazole with a magnesium source in a solution of an organic solvent,
   (b) partly removing said organic solvent,
   (c) isolating a magnesium salt of omeprazole containing up to 5 wt.-% of said organic solvent.

4. The process of claim 3, wherein the salt of omeprazole contains more than 95% of a salt of omeprazole and less than 5% of omeprazole.

5. The process of claim 4, wherein the salt of omeprazole contains more than 95% of omeprazole magnesium and less than 5% of omeprazole.

6. The process of claim 1, wherein the salt of omeprazole is a solid salt of omeprazole.

7. The process of claim 6, wherein the solid salt of omeprazole is crystalline.

8. The process of claim 7, wherein if omeprazole is S-omeprazole, the obtained solid is form B.

9. The process of claim 7, wherein the solid salt of omeprazole has a crystallinity of more than 70%.

10. The process of claim 7, wherein the solid salt of omeprazole has a crystallinity of less than 70%.

11. The process of claim 6, wherein the solid salt of omeprazole is amorphous.

12. The process of claim 1, wherein the organic solvent is a C1 to C4 alcohol or acetone.

13. The process of claim 3, wherein the magnesium source is magnesium alcoholate of a C1 to C4 alcohol.

14. The process of claim 12, wherein the C1 to C4 alcohol is methanol.

15. The process of claim 1, wherein omeprazole is S-omeprazole.

16. The process of claim 1, wherein omeprazole is a mixture of S-omeprazole and R-omeprazole in e.e. of more than 90%.

17. The process of claim 1, wherein the gas comprising water vapors is air or nitrogen comprising water vapors.

18. The process of claim 1, wherein the gas comprising water vapors is air or nitrogen saturated with water.

19. The process of claim 1, wherein step (i) is performed at room temperature.

20. The process of claim 1, wherein step (i) comprises blowing a gas comprising water vapors through a salt of omeprazole containing at least one organic solvent.

21. The process of claim 1, wherein the gas comprising water vapors is a gas stream comprising water vapors.

22. The process of claim 1, wherein omeprazole is a mixture of S-omeprazole and R-omeprazole in e.e. of more than 98%.

23. The process of claim 1, wherein omeprazole is a mixture of S-omeprazole and R-omeprazole in e.e. of more than 99.5%.

* * * * *